United States Patent [19]

Mari et al.

[11] Patent Number: 4,992,603

[45] Date of Patent: Feb. 12, 1991

[54] PROCESS FOR PRODUCING NITROMETHANE

[75] Inventors: Roger Mari, Villers-les-Nancy; Jacques Quibel, Maisons-Laffitte, both of France

[73] Assignee: S.E.P.P.I.C. Societe d'Exploitation de Produits pour les Industries Chimiques, Paris, France

[21] Appl. No.: 363,735

[22] Filed: Jun. 9, 1989

[30] Foreign Application Priority Data

Jun. 9, 1988 [FR] France .................................. 88 07675

[51] Int. Cl.$^5$ .............................................. C07C 205/02
[52] U.S. Cl. ...................................... 568/948; 568/947
[58] Field of Search ........................ 568/924, 947, 948

[56] References Cited

U.S. PATENT DOCUMENTS

| | | | |
|---|---|---|---|
| 3,780,115 | 12/1973 | Lhonore et al. | 568/948 |
| 3,869,253 | 3/1975 | Lhonore et al. | 568/947 X |
| 4,260,838 | 4/1981 | Lhonore et al. | 568/947 |
| 4,431,842 | 2/1984 | Hayes | 568/948 |
| 4,458,094 | 7/1984 | Sherwin | 568/948 X |
| 4,469,904 | 9/1984 | Wang et al. | |
| 4,476,336 | 10/1984 | Sherwin | 568/947 |
| 4,517,392 | 5/1985 | Wang et al. | 568/948 |
| 4,517,394 | 5/1985 | Wang et al. | 568/948 |
| 4,524,226 | 6/1985 | Wang et al. | 568/948 |
| 4,626,607 | 12/1986 | Jacquinot et al. | 568/948 |

FOREIGN PATENT DOCUMENTS

| | | |
|---|---|---|
| 0146203 | 8/1984 | European Pat. Off. |
| 0146204 | 8/1984 | European Pat. Off. |

*Primary Examiner*—Robert L. Stoll
*Assistant Examiner*—Valerie Fee
*Attorney, Agent, or Firm*—Browdy and Neimark

[57] ABSTRACT

Nitromethane is preparaed from a nitriding agent comprising an oxygenated nitrogen compound and a carbon compound containing two carbon atoms and at least one atom other than carbon and hydrogen.

11 Claims, No Drawings

PROCESS FOR PRODUCING NITROMETHANE

FIELD OF THE INVENTION

This invention pertains to the preparation of nitromethane.

BACKGROUND OF THE INVENTION

Many processes have been proposed for making nitromethane, especially by direct nitration of methane. However, it is commonly known that methane is much more difficult to nitrate than heavier hydrocarbons because it is more stable. Levels for converting methane into nitromethane are often still low.

Research has thus been conducted using common raw materials in the chemical industry in general to develop a process to make nitromethane other than by the methane procedure.

SUMMARY OF THE INVENTION

According to the invention, a process is proposed that uses as raw materials a nitriding agent made up of oxygenated nitrogen compounds and a carbon-containing compound having two carbon atoms and at least one atom other than carbon, as well as hydrogen to produce nitromethane.

Carbon compounds comprising two carbon atoms and at least one oxygen atom were found to produce considerable nitromethane yields compared to carbon compounds.

Carbon compounds may advantageously be ethanol, acetic acid or acetaldehyde.

The nitriding agent is selected from oxygenated nitrogen compounds such as nitric acid and nitrogen dioxide ($NO_2$), either used alone or in a mixture. The nitric acid concentration may be between 50 to 100% and, more advantageously, the commercially available concentration.

Moreover, nitromethane yields in proportion to the carbon compound are greater in the presence of a catalyst than when one is not present. Catalysts containing at least one chlorine atom are found to be very effective. The presence of dichloroethane is highly advantageous, especially when the reaction is catalyzed by this dichlorinated compound used in a molar proportion of approximately 0.2% to 1% of the carbon compound having two carbon atoms.

Results are influenced by the selected molar ratio of the carbon compound to the nitriding agent.

When the ratio between the number of carbon-containing molecules and the number of nitriding molecules is under 1, the process yields a nitromethane-rich mixture. If the carbon-containing agent is ethanol, a nitromethane-rich mixture is obtained having a considerable amount of acetic acid, which is converted to nitromethane in a subsequent step. This molar ratio is preferably between 0.2 and 0.9.

When the ratio between the number of carbon-containing molecules and the number of molecules of the nitriding agent is greater than 1, preferably from 1.2 to 1.5, nitromethane appears with the carbon-containing compound that did not react, and this compound is recycled for a later identical operation.

The nitriding reaction pressure is maintained at 1 to 30 bar, and reaction temperatures are between 220° C. and 500° C., preferably between 280° C. and 430° C. When the carbon-containing raw material is ethanol, the reaction temperature is advantageously between 290° C. and 330° C., and when the carbon-containing agent is acetic acid, this temperature range is 360° C. to 430° C.

Reaction contact time is a function of the temperature, pressure and composition of the mixture used to obtain the desired results. For example, a time of 10 to 12 seconds for the reaction using ethanol at 325° C. with an ethanol/nitriding agent ratio of approximately 1.3 produces a yield of approximately 60% in moles of nitromethane with respect to the alcohol consumed.

To obtain equivalent results, reaction time should be adjusted as a function of temperature. For example, with an optimal reaction time of 10.2 seconds, a pressure of 3 bar at 325° C., an ethanol/nitric acid ratio of 1.32 and a catalyst (dichloroethane) content of 0.3% produces a yield of 64.4% for a conversion rate of 13.4; when the temperature increases to 340° C., this optimum time drops to 8 seconds, and increases to 12.5 seconds at 310° C. However, under these conditions, the highest yield is obtained at 325° C.

Under identical reaction conditions, the presence of a catalyst improves the yield and conversion rate. For example, at 320° C. under a pressure of 3 bar, with an ethane/nitric acid ratio of 1.15, in the presence of 0.5% catalyst (dichloroethane), we obtain a yield of 31.6% and a conversion rate of 15.6%, while, in the absence of a catalyst, these quantified results are respectively 18.8% and 11.2%. However, in the absence of a catalyst, we note the appearance of 4% acetaldehyde and 1% acetic acid, convertible raw materials. In the presence of 0.3% catalyst, the results are substantially the same as those obtained with a content of 0.54%.

In order to change the reaction time, the reaction mixture can be diluted with a diluent that is inert with respect to the reagents and products of the reaction. The inert diluent can be nitrogen or water, added in the appropriate quantities for the desired modification.

DETAILED DESCRIPTION OF THE INVENTION

Below are examples illustrating the invention on a non-restrictive basis.

EXAMPLE 1

Nitromethane was formed from nitric acid (the nitriding agent) and ethanol (the oxygenated carbon compound), which were reacted in a molar ratio of 0.23 ethanol/nitric acid at a temperature of 310° C. under a pressure of 6 bar. The reaction was conducted in the presence of 0.3 mole % of dichloroethane per mole of ethanol. The reaction was allowed to continue for 9.2 seconds.

For 100 moles of ethanol used, 49 moles of nitromethane 10 and 55 moles of acetic acid were obtained. The remaining carbon products were in the form of carbon dioxide and carbon monoxide, predominantly carbon monoxide.

In this example, the ratio between the number of carbon-containing molecules and the number of nitriding molecules was less than 1, and the carbon-containing agent, ethanol, yielded a nitromethane-rich mixture containing a significant amount of acetic acid. This acetic acid was converted into nitromethane in a subsequent phase.

EXAMPLE 2

Nitromethane was formed from a mixture of ethanol and nitric acid in a molar ratio of 1.32 ethanol:nitric acid. The reactants were reacted at 320° C. under a pressure of 3 bar in the presence of 0.3 mole % of dichloroethane with respect to the ethanol.

For each 100 moles of ethanol used, 13.4 moles of nitromethane and 79 moles of ethanol were obtained. The remaining carbon was in the form of carbon dioxide and carbon monoxide, predominantly carbon monoxide.

This example illustrates a ratio between the number of nitriding molecules in excess of 1 wherein nitromethane appears with the remaining ethanol. The ethanol that did not react was recycled in an identical subsequent procedure.

EXAMPLE 3

Nitromethane was formed from acetic acid and nitric acid in an acetic acid/nitric acid molar ratio of 1.2. The reaction was conducted at 410° C. under a pressure of 6 bar for 10.5 seconds.

For each 100 moles of acetic acid used, 14 moles of nitromethane and 75 moles of acetic acid were formed. The remaining carbon was in the form of carbon dioxide and carbon monoxide, predominantly carbon monoxide.

This example illustrates an acetic acid/nitriding agent molar ratio in excess of 1, wherein the nitromethane appears with acetic acid that did not react. This unreacted acetic acid is recycled in a subsequent identical reaction.

EXAMPLE 4

Nitromethane was formed from a mixture of acetic acid and nitric acid in an acetic acid/nitric acid molar ratio of 0.24 reacted at a temperature of 390° C. under a pressure of 6 bar for 9.3 seconds in the presence of 0.3 mole % dichloroethane with respect to the acetic acid.

For 100 moles of acetic acid, 20 moles of nitromethane and 50 moles of acetic acid were obtained. The remaining carbon was in the form of carbon dioxide and carbon monoxide. This example illustrates an acetic acid/nitriding agent ratio of less than 1, wherein nitromethane appears in high proportions.

EXAMPLE 5

Acetaldehyde and nitric acid were reacted in an acetaldehyde/nitric acid molar ratio of 0.4 in the presence of 0.3 mole % dichloroethane with respect to the acetaldehyde. The reaction was conducted for ten seconds at 335° C. under a pressure of 6 bar.

For 100 moles of acetaldehyde, there was obtained 30 moles of nitromethane, 14 moles of acetic acid, and carbon dioxide and carbon monoxide, with the carbon monoxide predominating. This example illustrates an acetaldehyde/nitriding agent ratio of less than 1, wherein nitromethane was formed in a large quantity.

EXAMPLE 6

In this example, we studied the influence of temperature with a carbon compound/nitriding ratio in excess of 1 at a pressure of 3 bar, on the reaction of nitric acid and ethanol, with an ethanol/nitric acid ratio of 1.3 in the presence of 0.3% mole of dichloroethane with respect to ethanol, and a reaction time of 9.5 to 10.3 seconds.

The temperature was increased from 270° to 380° C.; the results obtained are provided in Table I below in molar yields of converted ethanol:

TABLE I

| Temperature | Nitromethane/ ethanol molar yield | Number of moles of converted ethanol |
|---|---|---|
| 270° C. | 9.7% | 6.9% |
| 315° C. | 48.8% | 13.3% |
| 325° C. | 64.4% | 13.4% |
| 340° C. | 58.9% | 12.9% |
| 365° C. | 49.1% | 12.2% |
| 380° C. | 7.5% | 3.5 |

EXAMPLE 7

In this example, we proceeded with the same type of study as above, with a carbon compound/nitriding agent molar ratio of less than 1.

Under a pressure of 6 bar, nitric acid and acetic acid in a molar ratio of 0.3 were allowed to react in the presence of 0.3% mole of dichloroethane with respect to acetic acid for 9.5 to 10.5 seconds.

The influence of temperature on the nitromethane yield and converted acetic acid appears in Table II below:

TABLE II

| Temperature | Nitromethane/ acetic acid molar yield | Number of moles of $CH_3COOH$ converted |
|---|---|---|
| 365° C. | 97.7% | 8.4% |
| 375° C. | 60.4% | 14.2% |
| 385° C. | 41.9% | 20.3% |
| 395° C. | 20.3% | 19.4% |
| 405° C. | 18.3% | 20.0% |
| 415° C. | 11.6% | 11.1% |

EXAMPLE 8

Study of the influence of pressure.

Pressure behaves as indicated in the table below when the temperature is 310° C.; the nitriding agent is nitric acid; the carbon-containing agent is ethanol; the ethanol/nitric acid molar ratio is 0.87%; the catalyst (0.3% mole/ethanol) is dichloroethane; reaction time is 10 seconds:

TABLE III

| Pressure | Nitromethane/ ethanol molar yield | Number of moles of $C_2H_5OH$ molecules converted |
|---|---|---|
| 3 bar | 11.3% | 10.7% |
| 5 bar | 18.3% | 13.0% |

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A process for preparing nitromethane comprising reacting an oxygen-containing nitriding agent with an oxocarbon containing raw material in the presence of a catalyst, wherein said raw material contains substantially exclusively said oxocarbon compound, said oxocarbon compound having two carbon atoms and at least one oxygen atom, and wherein the catalyst is dichloroethane.

2. The process for preparing nitromethane according to claim 1 wherein said oxocarbon compound is selected from the group consisting of ethanol, acetic acid, and acetaldehyde.

3. The process for preparing nitromethane according to claim 1 wherein said nitriding agent is selected from the group consisting of nitric acid, nitrogen dioxide, and mixtures thereof.

4. The process for preparing nitromethane according to claim 1 wherein said catalyst is used in molar proportions of from about 0.2 to 1 mole % with respect to the oxocarbon compound.

5. The process for preparing nitromethane according to claim 1 wherein the reaction temperature is from about 220° to about 500° C. and the reaction pressure is from about 1 to about 30 bar.

6. The process for preparing nitromethane according to claim 5 wherein the reaction temperature is from about 280° to about 430° C.

7. The process for preparing nitromethane according to claim 1 wherein the molar ratio of said oxocarbon compound to said nitriding agent is less than 1.

8. The process for preparing nitromethane according to claim 7 wherein the molar ratio of said oxocarbon compound to said nitriding agent is from about 0.2 to about 0.9.

9. The process for preparing nitromethane according to claim 1 wherein the molar ratio of said oxocarbon compound to said nitriding agent is greater than 1, and the remaining oxocarbon raw material is recycled.

10. The process for preparing nitromethane according to claim 9 wherein the molar ratio of said oxocarbon compound to said nitriding agent is from about 1.2 to about 1.5.

11. The process for preparing nitromethane according to claim 1 wherein the reaction mixture is diluted with a diluent that is inert with respect to the reactants and to the reaction products.

* * * * *